United States Patent
Maruyama

(10) Patent No.: US 8,317,685 B2
(45) Date of Patent: Nov. 27, 2012

(54) ROTATABLE OPERATION DEVICE FOR ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 930 days.

(21) Appl. No.: 12/358,499

(22) Filed: Jan. 23, 2009

(65) Prior Publication Data

US 2009/0192356 A1    Jul. 30, 2009

(30) Foreign Application Priority Data

Jan. 25, 2008  (JP) .................................. 2008-014402

(51) Int. Cl.
*A61B 1/00* (2006.01)

(52) U.S. Cl. ......... 600/146; 600/133; 600/147; 600/148

(58) Field of Classification Search ........... 600/146–152
See application file for complete search history.

(56) References Cited

U.S. PATENT DOCUMENTS

| | | | | |
|---|---|---|---|---|
| 4,207,873 | A * | 6/1980 | Kruy ............................. | 600/146 |
| 5,507,717 | A * | 4/1996 | Kura et al. ................... | 600/146 |
| 5,575,755 | A * | 11/1996 | Krauter et al. ................ | 600/148 |
| 6,656,111 | B2 * | 12/2003 | Fujii et al. .................... | 600/146 |
| 7,494,462 | B2 * | 2/2009 | Seki et al. .................... | 600/146 |
| 2001/0034472 | A1 * | 10/2001 | Fujii et al. .................... | 600/146 |
| 2007/0088353 | A1 | 4/2007 | Sugita | |
| 2007/0100205 | A1 | 5/2007 | Iriyama | |
| 2007/0198011 | A1 | 8/2007 | Sugita | |
| 2007/0255102 | A1 | 11/2007 | Maruyama | |
| 2007/0255103 | A1 | 11/2007 | Maruyama | |
| 2007/0255104 | A1 | 11/2007 | Maruyama | |
| 2007/0282326 | A1 | 12/2007 | Sugita | |
| 2007/0287887 | A1 | 12/2007 | Maruyama | |
| 2008/0319263 | A1 | 12/2008 | Maruyama | |

FOREIGN PATENT DOCUMENTS

| | | |
|---|---|---|
| JP | 7-180773 | 7/1995 |
| JP | 2002-555 | 1/2002 |
| JP | 2002-65576 | 3/2002 |
| JP | 2005-28018 | 2/2005 |

OTHER PUBLICATIONS

English language Abstract of JP 2005-28018, Feb. 3, 2005.
Japan Office action, dated Jun. 27, 2012 along with an english translation thereof.
Japan Office action, dated Sep. 7, 2012 along with an english translation thereof.

* cited by examiner

*Primary Examiner* — Matthew J Kasztejna
(74) *Attorney, Agent, or Firm* — Greenblum & Bernstein P.L.C.

(57) ABSTRACT

A rotatable operation device for an endoscope includes a fixed shaft projected outward from an operating portion, a cylindrical shaft projected from a rotatable operating member. The cylindrical shaft is rotatably fitted on the fixed shaft, and an end side surface of the cylindrical shaft contacts a fixed surface defined inside the operating portion. An internal space of the operating portion and an internal space of the rotatable operating member are airtight against outside. The rotatable operation device is configured to have an air passage which is formed in the cylindrical rotary shaft, a space at a fitted portion between the fixed shaft and the cylindrical rotary shaft communicating with the inside space of the operating portion through the air passage with the end side surface and the fixed surface remaining contacted.

3 Claims, 7 Drawing Sheets

ROTATABLE OPERATION DEVICE FOR ENDOSCOPE

BACKGROUND OF THE INVENTION

1. Technical Field

The present invention relates to a rotatable operation device for an endoscope.

2. Related Art

There are various forms of operation devices for operating a bendable portion of endoscopes. Many of such devices employ a mechanism which is configured such that a fixed shaft projects outward from an operating unit of the endoscope, and a cylindrical rotary shaft of an operation (rotatable) knob is fitted on the fixed shaft so that the cylindrical rotary shaft is rotatable about an axis thereof. Further, one end surface of the cylindrical rotary shaft is arranged to contact a stationary surface defined in the operating unit. An example of such a structure is disclosed in Japanese Patent Provisional Publication No. 2005-28018.

In endoscopes, the operating units have been formed to have a complete airtight structure (i.e., the internal space does not communicate with the outside) so that after-use cleaning, sterilization and the like can be performed completely. The operation knob has configured to have a certain internal space where a friction mechanism for stopping the operation knob at an arbitrary rotational position. Such an operation knob is also formed to be airtight.

In order to check the airtight configuration of the endoscope, a so-called a leak test is performed. The leak test is a test by injecting compressed air into the inside of an endoscope and then discharging it therefrom for inspecting existence of pinholes and the like, which may cause liquid leakage accidents.

FIGS. 6 to 9 illustrate processes of the leak test in sequence. As shown in FIG. 6, an operation unit of an endoscope is provided with a fixed shaft 92, which projects from an operating portion 91, and is formed to be airtight so that the internal space of the operating portion 91 does not communicate with the outside. Further, the operation unit is provided with an operation knob 94 having an internal space 93 and formed to be airtight so that the internal space 93 does not communicate with the outside. The operation unit has a cylindrical rotary shaft 95 which is rotatably fitted on the fixed shaft 92. One end surface of the cylindrical rotary shaft 95 contacts a fixing surface 96 defined inside the operating portion 91.

When the leak test is performed, as shown in FIG. 7, compressed air is injected through an open/close valve 97 communicating with the inside space of the operating portion 91. When the compressed air is injected through the open/close valve 97, the pressure inside the operating portion 91 increases. Then, the cylindrical rotary shaft 95 is moved outward along the axis, due to a play of its structure and due to a differential pressure between the pressure inside the operating portion 91 and the pressure in the internal space 93 of the operation knob 94 which initially had an atmospheric pressure.

The movement amount of the cylindrical rotary shaft 95, which moves from an initial position up to a position where the moving member comes into contact with a thrust stopper (not shown), is very small (e.g., approximately 0.1 to 0.2 mm). As the cylindrical rotary shaft 95 moves upward, a gap 98 is formed between the fixing surface 96 and the end surface of the cylindrical rotary shaft 95.

Consequently, as shown in FIG. 8, the compressed air is delivered from the space inside the operating portion 91 to the internal space 93 of the operation knob 94 through the gap 98 and a space formed an inter-fitting portion between the outer periphery of the fixed shaft 92 and the inner periphery of the cylindrical rotary shaft 95, whereby the pressure in the internal space 93 is increased. When the pressure in the internal space 93 reaches a predetermined value, the injection of the air is stopped, and it is examined whether leakage of the air occurs.

When the leak test is finished, as shown in FIG. 9, the open/close valve 97 is opened to reduce the pressure in the operating portion 91 to an atmospheric pressure. As the pressure is decreased, the cylindrical rotary shaft 95 is moved toward the operating portion 91 side (i.e., downward in FIG. 9) due to differential pressure between the pressure in the operating portion 91 and the pressure in the internal space 93 of the operation knob 94, which pressure has become higher than atmospheric pressure inside the operating portion 91. Accordingly, the end surface of the cylindrical rotary shaft 95 is press-contacted against the fixing surface 96, while frictional resistance and the like at a contact portion 100 between the operation knob 94 and its bearing member also become increased, whereby rotating operation of the operation knob 94 becomes heavy and its operability becomes low.

SUMMARY OF THE INVENTION

The compressed air in the internal space 93 of the operation knob 94 gradually deflates and goes into the operating portion 91, and the pressure in the internal space 93 of the operation knob 94 becomes approximately equal to the pressure in the operating portion 91 within a certain period of time, in 1 to 2 hours, for example. However, it is inconvenient for the user to use the endoscope with low operability during the period.

Aspects of the present invention are advantageous in that there is provide a rotatable operation device for an endoscope with excellent operability, without causing the heavy rotating operation on the operation knob as described above immediately after a leak test.

According to aspects of the invention, there is provided a rotatable operation device for an endoscope which includes a fixed shaft projected outward from an operating portion, a cylindrical shaft projected outward from a rotatable operating member. The cylindrical shaft is rotatably fitted on the fixed shaft, and an end side surface of the cylindrical shaft contacts a fixed surface defined inside the operating portion. An internal space of the operating portion and an internal space of the rotatable operating member do not communicate with outside (i.e., the operating portion is configured to have an airtight structure). The rotatable operation device is configured to have an air passage which is formed in the cylindrical rotary shaft, a space at a fitted portion between the fixed shaft and the cylindrical rotary shaft communicating with the inside space of the operating portion through the air passage with the end side surface and the fixed surface remaining contacted.

According to aspects of the present invention, the pressure difference between the internal space of the operation knob and the internal space of the operation unit is quickly resolved. Therefore, even immediately after the leak test, excellent operability of the operation knob may be achieved.

BRIEF DESCRIPTION OF THE ACCOMPANYING DRAWINGS

DETAILED DESCRIPTION OF THE EMBODIMENTS

Embodiments

Hereinafter, referring to the accompanying drawings, embodiments of the present invention will be described in detail.

Figures 2, 3:
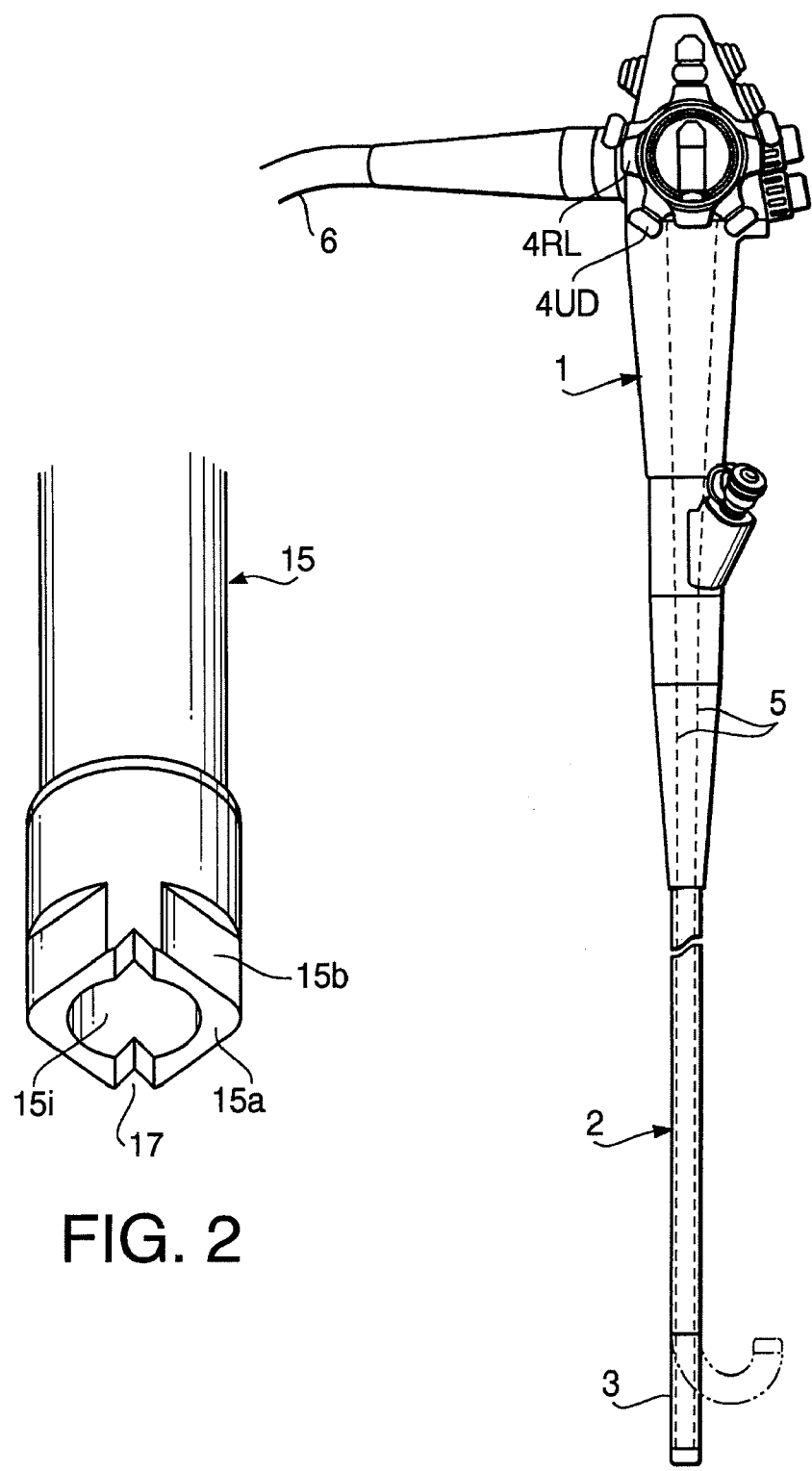
FIG. 2 is a partial perspective view of a cylindrical rotary shaft according to the first embodiment of the invention.
FIG. 3 is an external view of the endoscope according to the first embodiment of the invention.

FIG. 3 shows an appearance of an endoscope, which is provided with a bending portion 3 in the area close to the distal end of an inserting portion 2 of a flexible tube connected to the lower end of an operating portion 1. A user can bend the bending portion 3 arbitrarily in a desired direction by a desired angle remotely by operating the operating portion 1.

The operating portion 1 is provided with an up-and-down operation knob 4UD and a right-and-left operation knob 4RL arranged outside the operating portion 1. The operation knobs 4UD and 4RL are configured to be independently rotatable. When each of the operation knobs 4UD and 4RL is rotationally operated, a plurality of operating wires 5 are selectively pulled, whereby the bending portion 3 is bent.

A connecting flexible tube 6 extending backward from the rear surface of the operating portion 1 is provided with a connector (not shown) to be connected to a video processor, which also functions as a light-source unit, at an another end thereof. The endoscope as above is formed to be airtight (i.e., inside and outside of the endoscope do not communicate with each other) while the inside is wholly communicative, and is provided with a known open/close valve through a connector.

Figure 1:
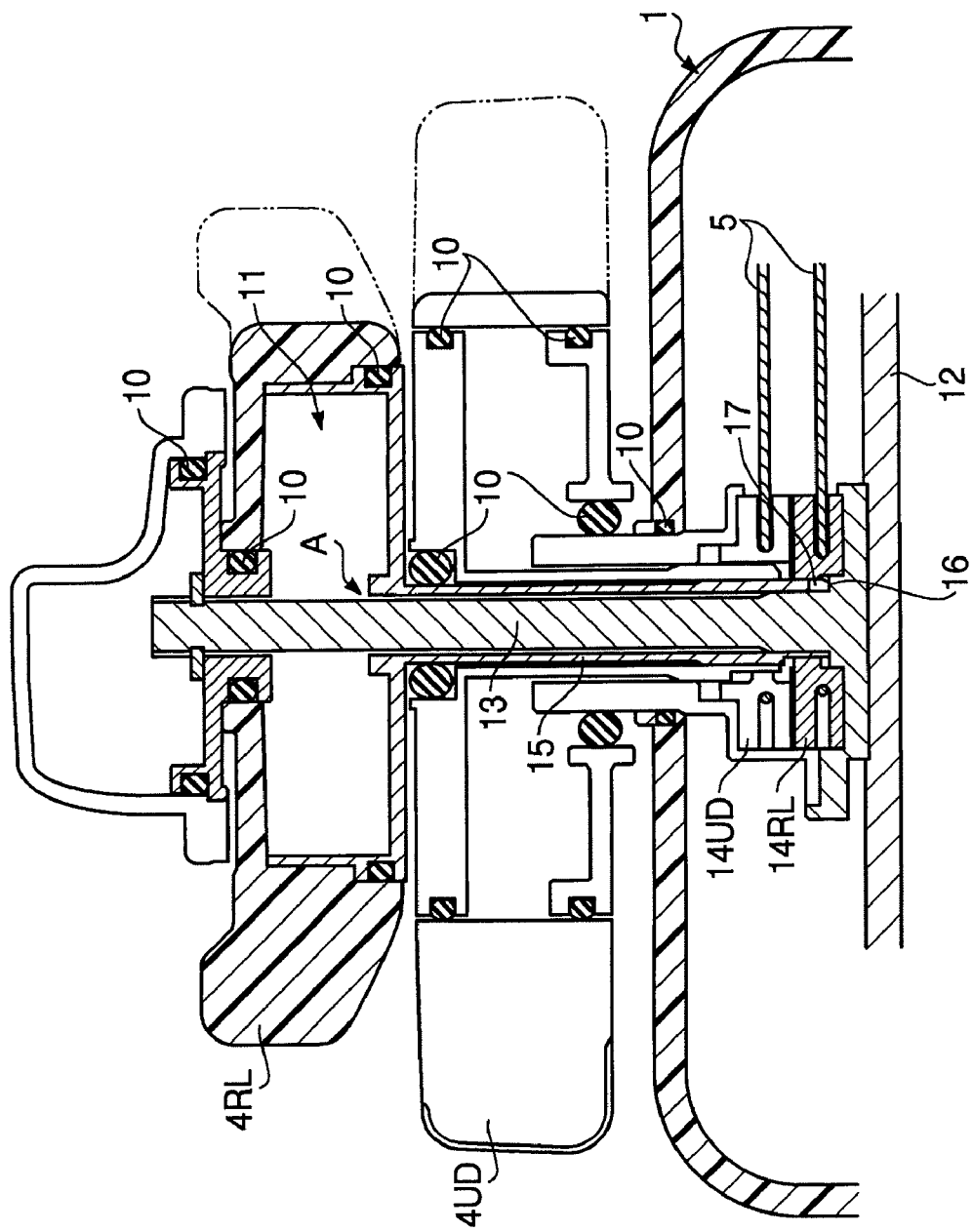
FIG. 1 is a vertical cross sectional view of a rotatable operation device for an endoscope according to a first embodiment of the invention.

FIG. 1 shows the rotatable operation device provided in the operating portion 1, in which hatched parts in the cross-sectional surface represent members closely related to the invention, and configuration on the other portions are simplified for brevity. O-rings 10 are attached at respective portions in the operation device for sealing, whereby not only the operating portion 1 but also the other spaces such as each space in the operation knobs 4UD and 4RL is formed not to communicate with the outside.

A friction mechanism is disposed in the internal space 11 of the operation knob 4RL for stopping the operation knob 4RL at an arbitrary rotational position. Since such a friction mechanism is well known, illustration is omitted for brevity.

A fixed shaft 13 provided to project outward from the operating portion 1 is fixedly mounted at the base end thereof on a frame 12 which is fixedly disposed in the operating portion 1, and the operating wires 5 are individually wound at each base end portion thereof around an up-and-down bending operation pulley 14UD and a right-and-left bending operation pulley 14RL which are rotatably disposed around the fixed shaft 13 in the operating portion 1.

The numeral 15 denotes a cylindrical rotary shaft which connects the operation knob 4RL with the bending operation pulley 14RL, and the cylindrical rotary shaft 15 rotatably covers and fits on the fixed shaft 13 around the axis line thereof, and the inner end surface is in abutting contact with a fixing surface 16 in the operating portion 1.

FIG. 2 shows in the vicinity of the inner end portion of the cylindrical rotary shaft 15, and 15i denotes a fitting hole which fits on the fixed shaft 13, 15a denotes the inner end surface which contacts the fixing surface 16 in the operating portion 1, and 15b denotes a square shank portion which engages with the operation pulley 14RL.

The numeral 17 is an air passage for allowing fitted portion (i.e., the fitting hole 15i) between the fixed shaft 13 and the cylindrical rotary shaft 15 to communicate with the inside of the operating portion 1, wherein the air passage 17 is formed in the shape of a notch, such as V-shape, which is formed by partially cutting out a contact surface (i.e., end side surface 15a) of the cylindrical rotary shaft 15 with respect to the fixing surface 16 in the operating portion 1.

Since the air passage 17 is formed, even when a compressed air is left in the internal space 11 of the operation knob 4RL and differential pressure from the pressure in the operating portion 1 which has an atmospheric pressure, air in the internal space 11 is quickly discharged and goes into the operating portion 1 through the space in the inter-fitting portion between the fixed shaft 13 and the cylindrical rotary shaft 15, as indicated with an arrow A in FIG. 1, and through the air passage 17. Consequently, the pressure in the internal space 11 becomes equal to the pressure in the operating portion 1, whereby the rotating operation on the operation knob 4RL will not become heavy.

Figure 4:
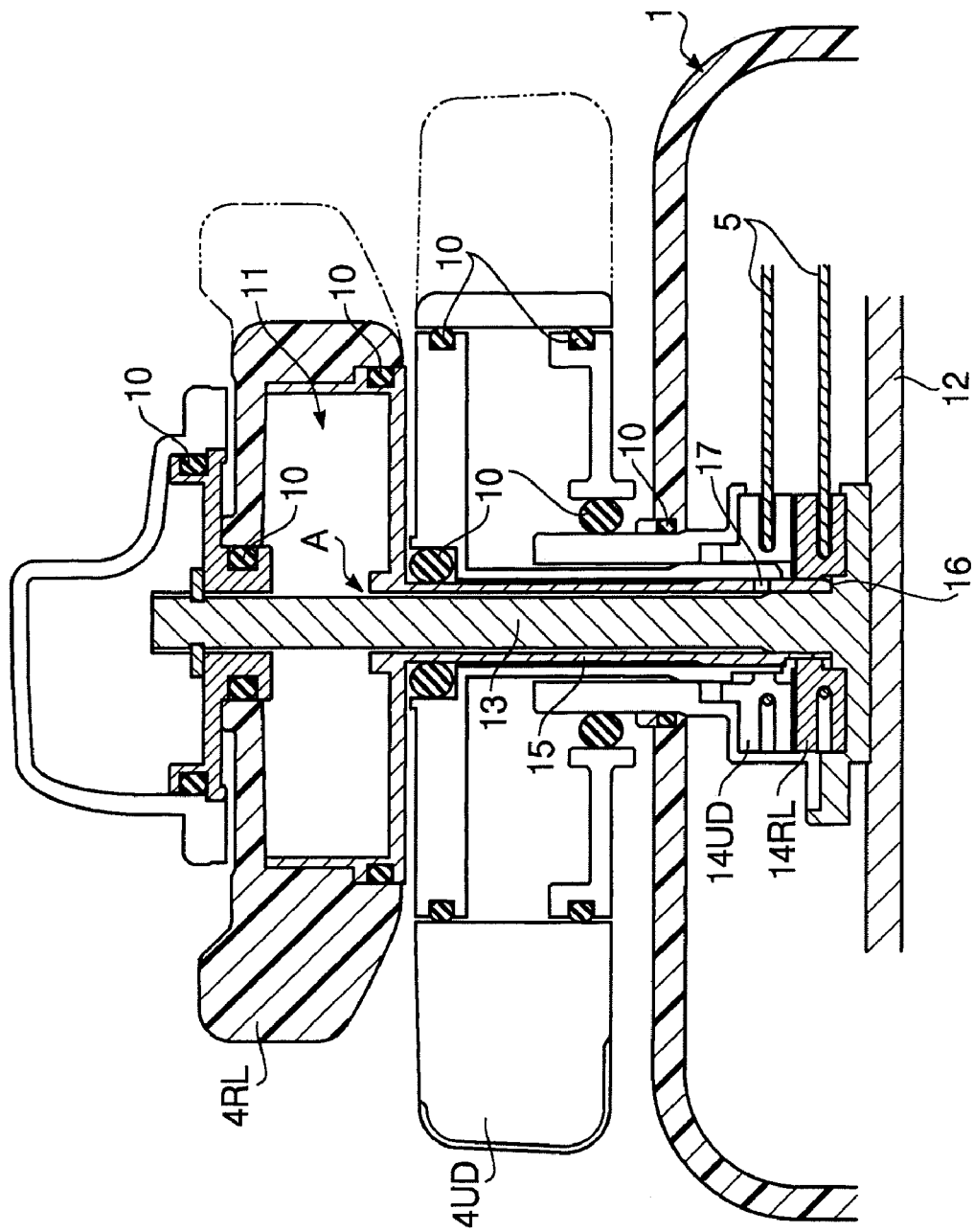
FIG. 4 is a vertical cross sectional view of a rotatable operation device for an endoscope according to a second embodiment of the invention.
Figure 5:
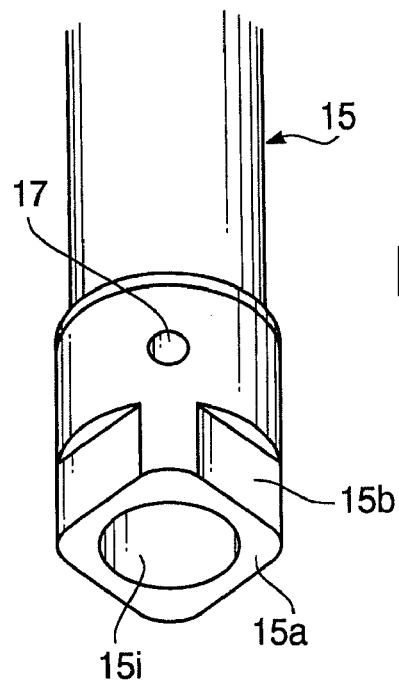
FIG. 5 is a partial perspective view of a cylindrical rotary shaft according to the second embodiment of the invention.
Figure 6:
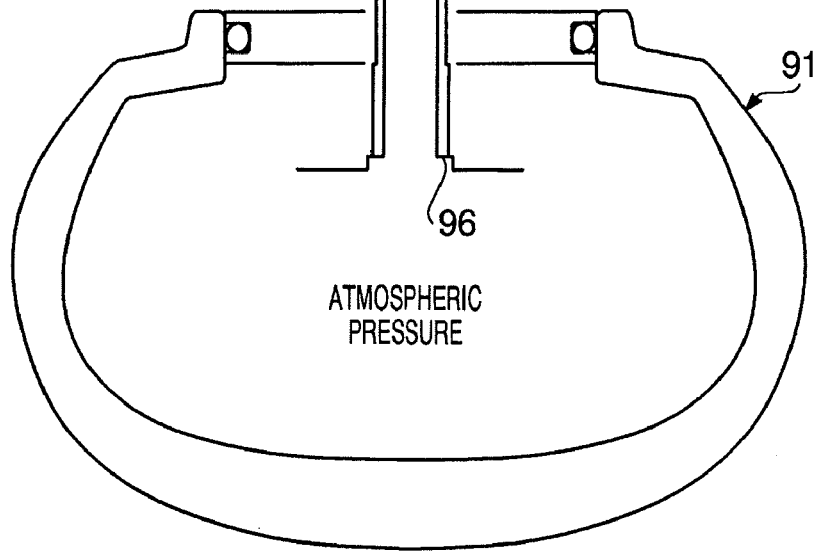
FIG. 6 is a schematic view for illustrating operation of a conventional bending operation device of an endoscope.
Figure 7:
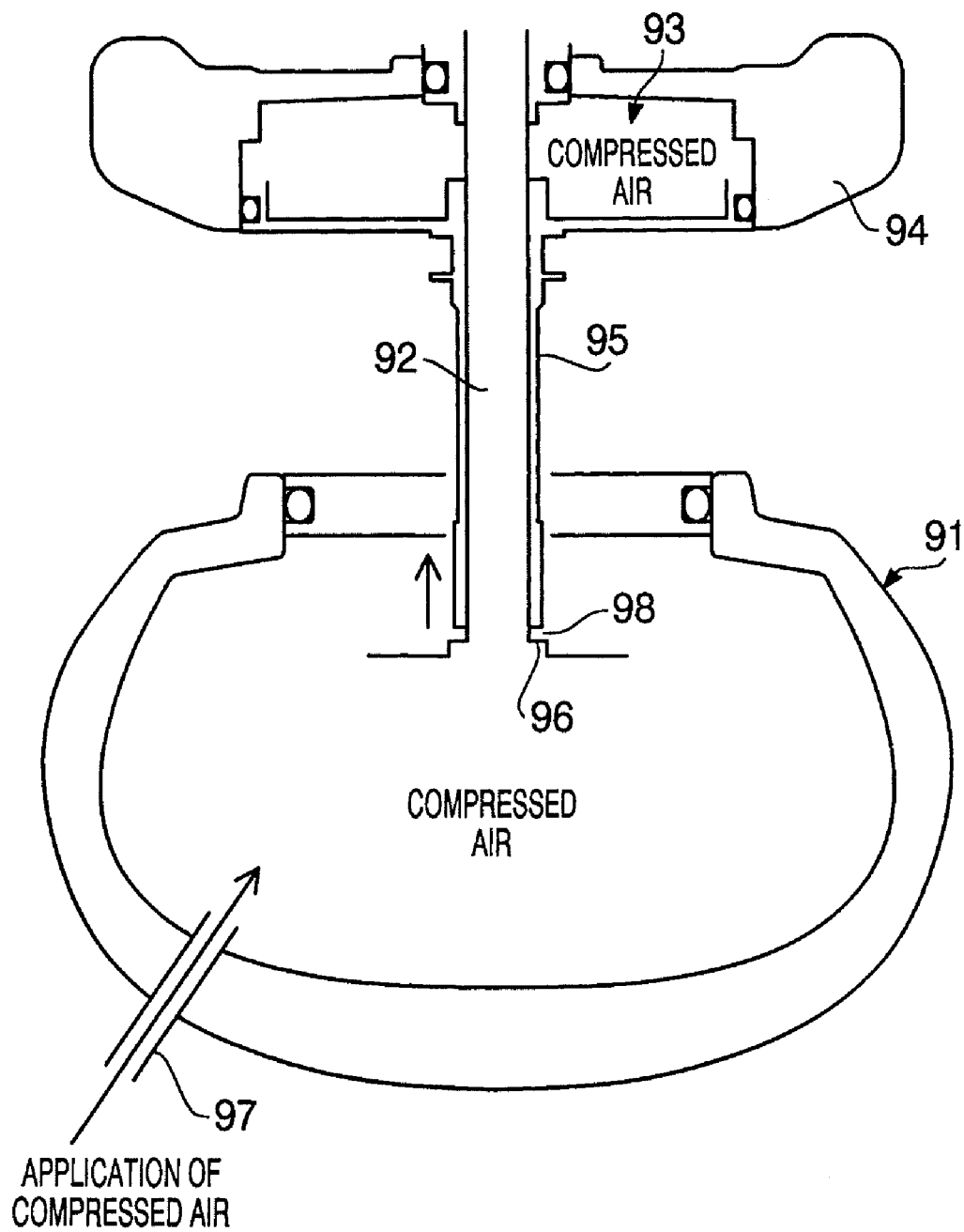
FIG. 7 is a schematic view for illustrating operation of the conventional bending operation device of an endoscope.
Figure 8:
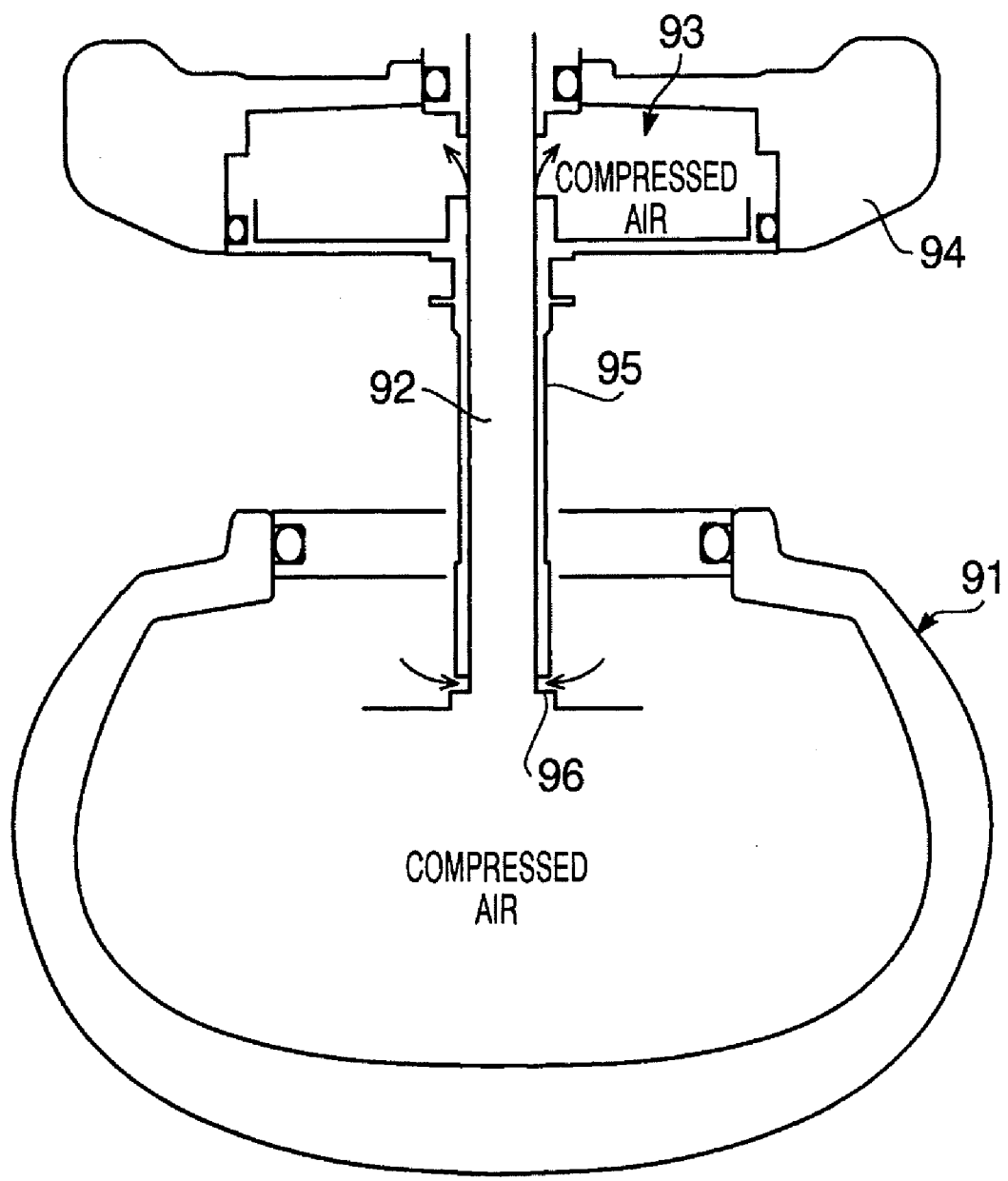
FIG. 8 is a schematic view for illustrating operation of the conventional bending operation device of an endoscope.
Figure 9:
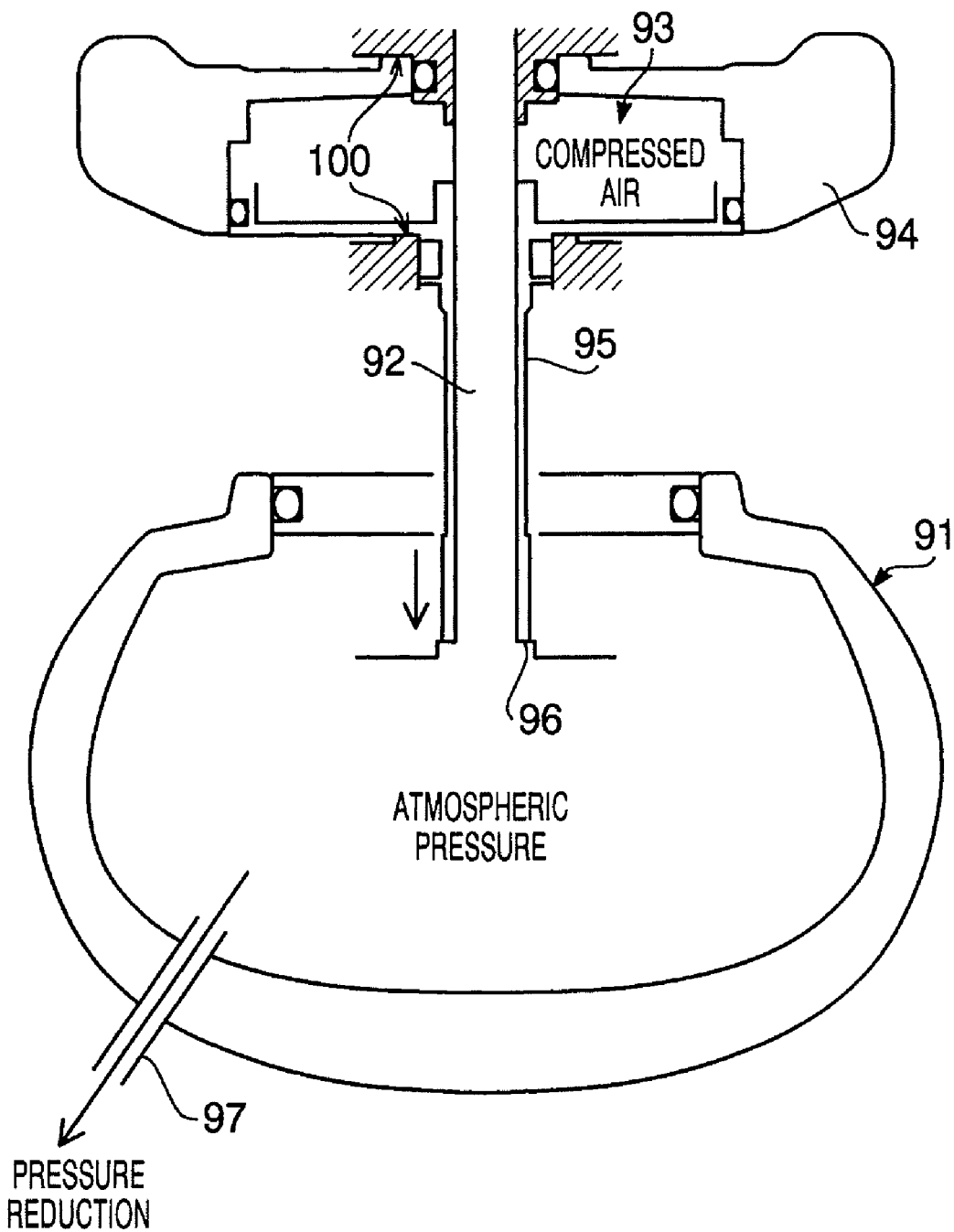
FIG. 9 is a schematic view for illustrating operation of the conventional bending operation device of an endoscope.

FIG. 4 and FIG. 5 show an operation device for an endoscope according to a second embodiment of the invention. According to the second embodiment, the air passage 17 is formed in the shape of through holes formed in the sidewall portion of the cylindrical rotary shaft 15 located in the operating portion 1. The fitting portion (i.e., the hole 15i) between the fixed shaft 13 and the cylindrical rotary shaft 15 is allowed to communicate with the inside space of the operating portion 1 through the air passage 17 (one or more through hole). According to the second embodiment, the similar effects to those of the first embodiment can be achieved.

In addition, the present invention is not to be limited to the embodiments described above, and further aspects or changes may be adopted, for example, the invention may be applied to the mechanism on the up-and-down operation knob 4UD side.

The present disclosure relates to the subject matter contained in Japanese Patent Application No. P2008-014402, filed on Jan. 25, 2008, which is expressly incorporated herein by reference in its entirety.

What is claimed is:

1. A rotatable operation device for an endoscope, comprising:

a fixed shaft projected outward from an operating portion;

a cylindrical shaft projected from a rotatable operating member, the cylindrical shaft being rotatably fitted on the fixed shaft, the cylindrical shaft having a proximal end portion extending from the rotatable operating member and a distal end portion positioned within the operating portion, and an end side surface of the distal end portion of the cylindrical shaft contacting a fixed surface defined inside the operating portion, the operating portion having an airtight structure so that an internal space of the operating portion and an internal space of the rotatable operating member do not communicate with an outside; and an air passage defined by an opening that penetrates an outer surface and an inner surface of the cylindrical shaft, the air passage being provided at the distal end portion of the cylindrical shaft, and an annular space provided between the fixed shaft and the cylindrical shaft, the annular space communicating with the internal space of the operating portion through the air passage with the end side surface and the fixed surface contacting each other.

2. The rotatable operation device for an endoscope according to claim 1, wherein the air passage is provided as a partial cut-out formed in the end side surface of the cylindrical shaft.

3. The bending operation device for an endoscope according to claim 1, wherein the air passage is formed in the shape of a through hole.

* * * * *